US00PP09044P

United States Patent [19]

Kordes

[11] Patent Number: Plant 9,044

[45] Date of Patent: Jan. 17, 1995

[54] HYBRID TEA ROSE PLANT NAMED KORIGNALE

[75] Inventor: Wilhelm Kordes, Sparrieshoop, Germany

[73] Assignee: Bear Creek Gardens, Inc., Medford, Oreg.

[21] Appl. No.: 241,493

[22] Filed: May 12, 1994

[51] Int. Cl.[6] ..... A01H 5/00

[52] U.S. Cl. ..... Plt./18

[58] Field of Search ..... Plt. 11, 14, 18

*Primary Examiner*—Howard J. Locker
*Attorney, Agent, or Firm*—Klarquist Sparkman Campbell Leigh & Whiston

[57] ABSTRACT

A Hybrid Tea Rose plant having attractive, porcelain pink, high-centered flowers; long, straight stems; long vase life, and large flowers.

1 Drawing Sheet

The present invention relates to a new and distinct variety of rose plant of the Hybrid Tea class which was originated by me by crossing an unnamed seedling (unpatented) with the variety KORprill (unpatented).

The primary objective of this breeding was to produce a new rose variety having the long stems, urn-shaped hybrid tea flowers and good cut-flower forcing ability of the male parent combined with the vigor and excellent flower form of the female parent. The objective was substantially achieved, along with other desirable improvements, as evidenced by the following unique combination of characteristics that are outstanding in the new variety and that distinguish it from its parents, as well as from all other varieties of which I am aware:

1. Large flower size;
2. Long stems;
3. Attractive porcelain pink flower color;
4. High-centered flower form; and
5. Long vase life.

Asexual reproduction of this new variety by budding, as performed at Wasco, Calif. and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—As unnamed seedling (unpatented).

*Pollen parent.*—KORprill (unpatented).

Classification:

*Botanical.*—*Rosa hybrida.*

*Commercial.*—Hybrid Tea.

FLOWER

Observations made from specimens grown in a greenhouse environment at Sparrieshoop, Germany and at Somis, Calif., from October, 1993, through November, 1994.

Blooming habit: Continuous.

Bud:

*Size.*—1½–1¾ inches long when the petals start to unfurl.

*Form.*—The bud form is long, pointed ovoid.

*Color.*—When sepals first divide, bud color is Yellow-White Group 158B. When half blown, the upper sides of the petals are principally White Group 155D with Red Group 36D as a blush on the petal edges, the lower third being Yellow Group 4D. The lower sides of the petals are White Group 155D with Red Group 36D as a blush on the petal edges, the lower third being Green-White Group 157A.

*Sepals.*—Color: Green Group 138B. Surface texture: Covered in fine hairs. There are three normally appendaged sepals. There are two unappendaged sepals with hairy edges.

*Receptacle.*—Color: Green Group 137D. Shape: Funnel. Size: Large, long (½ inch long×⅜ inch wide). Surface: Smooth.

*Peduncle.*—Length: Medium (3 inches). Surface: Smooth. Color: Light green. Strength: Stiff, erect.

Bloom:

*Size.*—Large. Average open size is 4–4½ inches.

*Borne.*—Singly.

*Stem.*—Long, strong. Average length is about 24–28 inches.

*Form.*—When first open: High centered. Permanence: Retains its form to the end, all petals curl, quill fashion.

*Petalage.*—Number of petals under normal conditions: 30.

*Color.*—The upper sides of the petals are principally White Group 155D with the outer portion showing a blush of Red Group 36D, the lower third being Yellow Group 4D. The reverse sides of the petals are White Group 155D with a blush of Red Group 36D on the petal edges, the lower third being Green-White Group 157A. The base of each petal is Yellow Group 4D. The major color on the upper side is White Group 155D.

*Variegations.*—None.

*Discoloration.*—The general tonality at the end of the first day: No change. At the end of the third day: No change.

*Fragrance.*—Slight.

Petals:

*Texture.*—Thick, leathery.

*Shape.*—Round.

*Form.*—Tips slightly recurved, edges slightly quilled.

*Arrangement.*—Imbricated, with a few small petaloids in the center.

*Persistence.*—Drop off cleanly.

*Lastingness.*—On the plant: Long (7–8 days). As a cut flower: Long (9–10 days).

Reproductive parts:

*Anthers.*—Size: Large. Quantity: Many. Color: Light yellow. Arrangement: Regular around styles.

*Filaments.*—Color: White.

*Pollen.*—Color: Lemon yellow.

*Styles.*—Color: Reddish.

*Stigmas.*—Color: Greenish white.

Form: Bush.

Growth: Vigorous, upright, branching. Height in one year in a greenhouse is 6 feet and the width is 3½ feet.

Foliage:

*Number of leaflets on normal mid-stem leaves.*—5.

*Size.*—Large (6 inches long×5 inches wide).

*Quantity.*—Abundant.

*Color.*—New foliage: Lower Side: Greyed-Purple Group 184A. Upper Side: Greyed-Purple Group 184A. Old foliage: Lower Side: Green Group 138A. Upper Side: Green Group 137A.

Leaflets:

*Shape.*—Pointed oval.

*Texture.*—Upper side: Leathery, glossy.

*Edges.*—Serrated.

*Serration.*—Single, small.

*Petiole rachis.*—Color: Reddish.

*Petiole underside.*—Smooth, with occasional prickles.

*Stipules.*—Medium (½ inch), serrated, bearded.

*Disease resistance.*—Resistant to mildew under normal growing conditions at Somis, Calif. Not tested for other fungal diseases.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜ inch), hooked downward.

*Color when young.*—Red.

Small prickles:

*Quantity.*—On main stalks: None.

*On laterals: None.*

I claim:

1. A new and distinct variety of rose plant of the Hybrid Tea class, substantially as herein shown and described, characterized particularly as to novelty by the unique combination of its attractive, porcelain pink, high-centered flowers; its long, straight stems; its long vase life, and its large flower size.

* * * * *

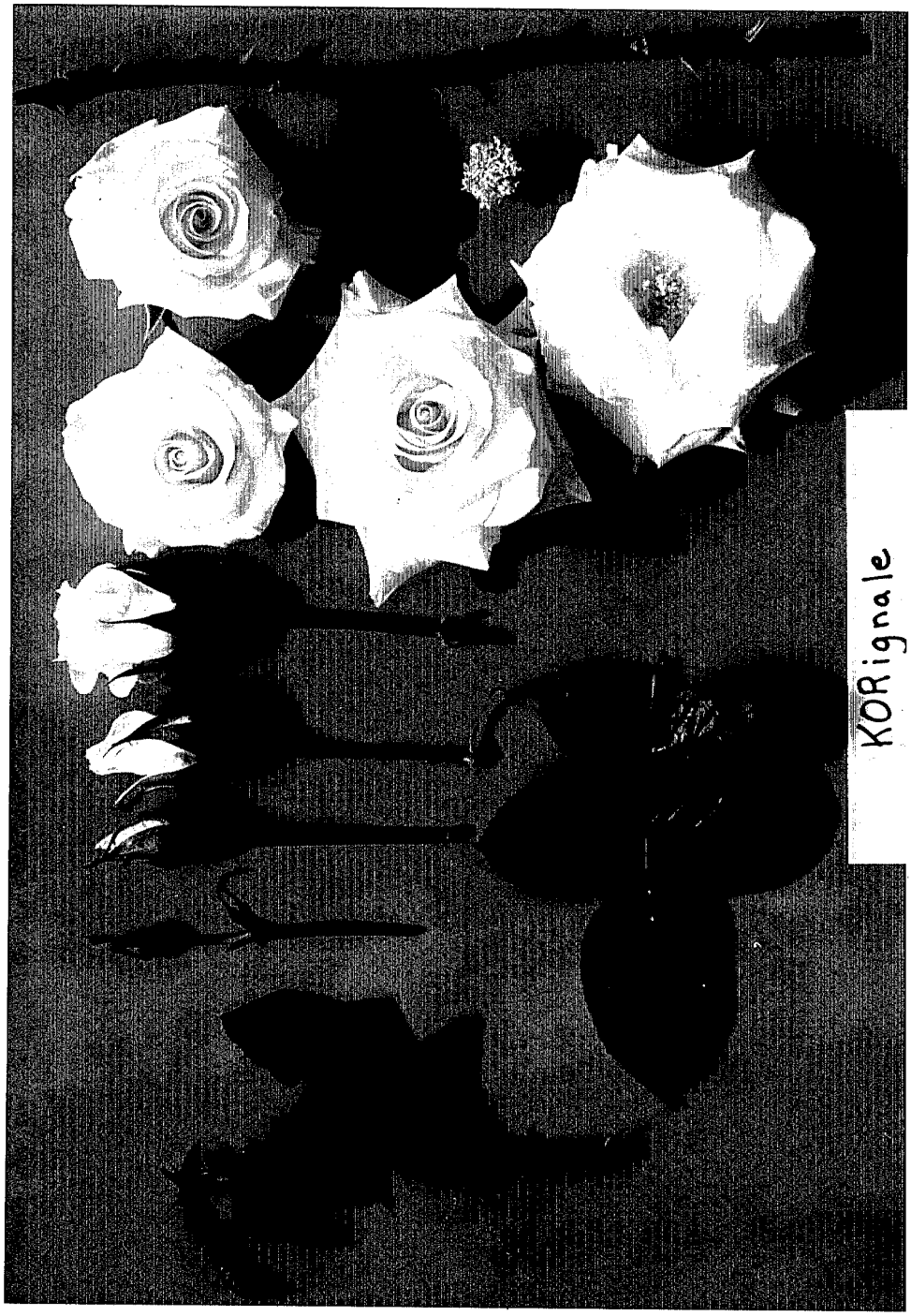
KORignale